(12) United States Patent
Gatlin

(10) Patent No.: US 7,211,665 B2
(45) Date of Patent: May 1, 2007

(54) SULFIDE SCAVENGER

(75) Inventor: Larry W. Gatlin, Floresville, TX (US)

(73) Assignee: Clearwater International, L.L.C., Houston, TX (US)

( * ) Notice: Subject to any disclaimer, the term of this patent is extended or adjusted under 35 U.S.C. 154(b) by 533 days.

(21) Appl. No.: 10/291,461

(22) Filed: Nov. 8, 2002

(65) Prior Publication Data

US 2003/0089641 A1    May 15, 2003

Related U.S. Application Data

(60) Provisional application No. 60/345,847, filed on Nov. 9, 2001.

(51) Int. Cl.
*C07D 251/04* (2006.01)
*C10G 29/00* (2006.01)
*C10G 29/20* (2006.01)

(52) U.S. Cl. ............... 544/180; 423/200; 423/228; 208/207; 208/237

(58) Field of Classification Search ............ 544/180; 423/220, 228, 200; 208/207, 237
See application file for complete search history.

(56) References Cited

U.S. PATENT DOCUMENTS

| | | |
|---|---|---|
| 2,149,380 A | 3/1939 | Yabroff et al. |
| 2,783,205 A | 2/1957 | Brooks et al. |
| 3,053,757 A | 9/1962 | Bloembergen |
| 4,266,054 A | 5/1981 | Au |
| 4,430,196 A | 2/1984 | Niu |
| 4,440,649 A | 4/1984 | Loftin et al. |
| 4,675,169 A | 6/1987 | Hass |
| 4,978,366 A | 12/1990 | Weers |
| 4,978,512 A | 12/1990 | Dillon |
| 5,074,991 A | 12/1991 | Weers |
| 5,128,059 A | 7/1992 | Storey et al. |
| 5,169,411 A | 12/1992 | Weers |
| 5,223,127 A | 6/1993 | Weers et al. |
| 5,266,185 A | 11/1993 | Weers et al. |
| 5,284,576 A | 2/1994 | Weers et al. |
| 5,347,004 A | 9/1994 | Rivers et al. |
| 5,354,453 A | 10/1994 | Bhatia |
| 5,405,591 A | 4/1995 | Galloway |
| 5,415,785 A | 5/1995 | Braden et al. |
| 5,462,721 A | 10/1995 | Pounds et al. |
| 5,486,605 A | 1/1996 | Gatlin |
| 5,488,103 A | 1/1996 | Gatlin |
| 5,498,707 A | 3/1996 | Gatlin |
| 5,554,349 A | 9/1996 | Rivers et al. |
| 5,567,213 A | 10/1996 | Gentry et al. |
| 5,674,377 A | 10/1997 | Sullivan et al. |
| 5,688,478 A | 11/1997 | Pounds et al. |
| 5,697,443 A | 12/1997 | Brezinski et al. |
| 5,698,171 A | 12/1997 | Trauffer et al. |
| 5,744,024 A | 4/1998 | Sullivan et al. |
| 5,958,352 A | 9/1999 | Callaway et al. |
| 6,024,866 A | 2/2000 | Weers et al. |
| 6,063,346 A | 5/2000 | Luna |
| 6,117,310 A | 9/2000 | Rivers |
| 6,136,282 A | 10/2000 | Fisher |
| 2002/0157989 A1 | 10/2002 | Gatlin et al. |

FOREIGN PATENT DOCUMENTS

| | | |
|---|---|---|
| CA | 2125513 | 1/1995 |
| CA | 2005946 | 2/1995 |
| CA | 2148849 | 12/1995 |
| DE | 24 04 511 A | 8/1975 |
| DE | 40 27 300 A1 | 3/1992 |
| GB | 1 456 732 | 11/1976 |
| GB | 2 245 588 A | 8/1992 |
| WO | WO-92/01481 | * 2/1992 |

OTHER PUBLICATIONS

W. J. Kauffman, "Observations on the Synthesis and Characterization of N,N',N"-Tris(dimethylaminopropyl)hexahydro-s-triazine and isolable intermediates," J. Heterocyclic Chemistry, p. 409-411, (Apr. 1, 1975).

Fuchslueger, Ulf et al, "Capillary Supercritical Fluid Chromatography/Mass Spectrometry of Phenolic Mannich Bases with Dimethyl Ether Modified Ethane as the Mobile Phase," Analytical Chemistry, American Chemical Society, vol. 71 (No. 13), p. 2324-2333, (Jul. 1, 1999).

GB Examination Report, Application No. GB0328368.6, dated Nov. 14, 2005.

* cited by examiner

*Primary Examiner*—Venkataraman Balasubramanian
(74) *Attorney, Agent, or Firm*—Patterson & Sheridan, L.L.P.

(57) ABSTRACT

1,3,5-($2H_2$,$4H_2$,$6H_2$) tripropanediamine N,N,N',N',N",N" hexamethyl is used to scavenge sulfur compounds from hydrocarbons. A novel method of making the triazine comprises autocondensing $(CH_3)_2NCH_2CH_2CH_2N\!=\!CH_2$.

25 Claims, No Drawings

SULFIDE SCAVENGER

RELATED APPLICATION

This application claims the full benefit of U.S. Provisional Patent Application No. 60/345,847, filed Nov. 9, 2001, having the same title, which is incorporated herein in its entirety.

TECHNICAL FIELD

This invention relates to the treatment of hydrocarbons and other compositions to remove sulfides therefrom. Compositions and methods are disclosed for the treatment of newly recovered crude oil, natural gas and the like to ameliorate the odors and other problems caused by the presence of sulfides such as hydrogen sulfide. The compositions can also be used to treat sulfides in sewage, pulp and paper manufacturing systems, and similar industrial fluids and suspensions.

BACKGROUND OF THE INVENTION

Various compositions have been proposed and used for the treatment of hydrocarbons to remove or otherwise treat hydrogen sulfide and/or other sulfides present in them. See, for example, Gatlin's U.S. Pat. Nos. 5,128,049, 5,486,605, 5,488,103, and 5,498,707, U.S. Pat. No. 4,978,512 in the name of Dillon, and Stanchem's Canadian Patent 2,269,476.

The treating agents for the removal of sulfides are often referred to as scavengers in the patent literature. Frequently the compositions are reaction products of aldehydes and amine compounds, and may or may not contain one or more triazines or derivatives thereof. See the descriptions in columns 5–8 of Trauffler et al. U.S. Pat. No. 5,698,171, Sullivan III et al. U.S. Pat. Nos. 5,674,377, 5,674,377 and 5,744,024, Rivers et al. U.S. Pat. No. 5,554,591, Weers et al. U.S. Pat. Nos. 5,074,991, 5,169,411, 5,223,127, 5,266,185, 6,024,866 and 5,284,576, Pounds et al. U.S. Pat. Nos. 5,462,721 and 5,688,478, Bhatia et al. Canadian patents 2,125,513 and 2,148,849, and Callaway U.S. Pat. No. 5,958,352. They may be contacted with the hydrocarbons in various ways as mentioned in these patents and others such as Galloway U.S. Pat. No. 5,405,591 and Fisher U.S. Pat. No. 6,136,282. Note that Callaway's ('352) trimer has the structure:

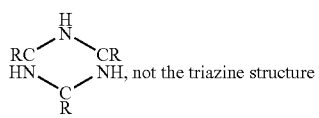

,not the triazine structure

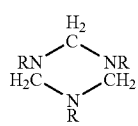

Sexton's GB patent 2,245,588 (p. 14) suggests the use of a reaction product of dimethylaminopropylamine and paraformaldehyde to treat fuel oils to prevent color and sediment formation. See also the triazines said to be useful for removing $H_2S$ in petroleum liquid, in Bhatia's U.S. Pat. No. 5,354,453. All of the patents identified in this paragraph and the preceding one are incorporated entirely by reference, as my invention may include the use of any of the sulfide scavengers recited or identified in them, particularly those containing at least one nitrogen, as a complement to the invention described herein.

The above cited references do not utilize the triazine compound described below to remove sulfides from hydrocarbons.

Many of the scavengers mentioned in the above cited patents remain, in one form or another, in the hydrocarbons they are used to treat. That is, they may be effective at suppressing the evolution of hydrogen sulfide, for example, but the sulfur is left in the hydrocarbon. There is a need for a method of treating hydrocarbons which does not merely neutralize the sulfur compounds, but enables the ready removal of them from the hydrocarbons.

SUMMARY OF THE INVENTION

My invention employs a triazine of the structural formula:

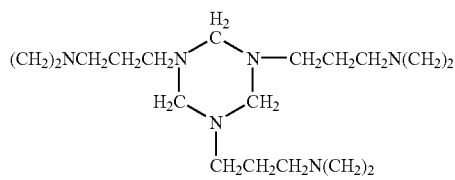

for the treatment of hydrocarbons to remove sulfides and other sulfur compounds. This triazine is sometimes described herein as 1,3,5-($2H_2,4H_2,6H_2$) tripropanediamine N,N,N',N',N",N" hexamethyl, and may sometimes be known as S-triazine, 1,3,5-tris[(3-dimethylamine)propyl] hexahydro. The compound may be referred to herein as "TPDAHM triazine" for tripropyldiaminehexamethyl. Unlike the tertiary butyl triazines used by Sullivan et al. in U.S. Pat. No. 5,674,377, this triazine may be described as hydrophilic. It not only attracts the target sulfur compounds in the hydrocarbons, but also can be separated from the hydrocarbon after associating with the sulfur compounds, by contact with water, thereby facilitating the permanent removal of the sulfur compound from the hydrocarbon. This effect may be compared with the use of Sullivan et al.'s hydroxyalkyl hexahydro triazines (prepared by the reaction of an alkanol amine and formaldehyde—U.S. Pat. No. 5,744,024 at col. 5, lines 29–30). Sullivan's material is also apparently hydrophilic but Sullivan et al. demonstrate it is ineffective without the concurrent use of an accompanying ammonium compound.

My invention includes a novel method of making TPDAHM triazine by the autocondensation of the compound $(CH_3)_2N\ CH_2\ CH_2\ CH_2\ N=CH_2$.

DETAILED DESCRIPTION OF THE INVENTION

My scavenger may be made by reacting dimethylaminopropylamine with formaldehyde (preferably paraformaldehyde):

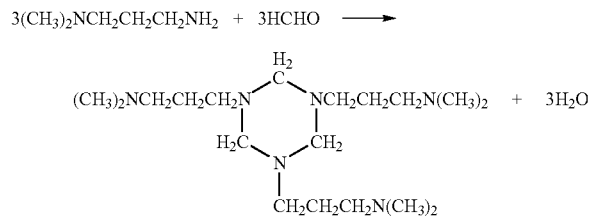

The formaldehyde may be used in excess; in the above formula, for example, the expression 3HCHO may read 3–6HCHO—that is, the formaldehyde may be used in a molar ratio to the amine of 1:1 to 2:1, 3:1 or more, i.e., as much as a 10:1 ratio of formaldehyde to amine may be appropriate. See pages 13 and 14 of GB 2,245,588A for a description of a preferred synthesis. One mole of the dimethylaminopropylamine (DMAPA) is dissolved in toluene and stirred. One mole of paraformaldehyde is added. The reaction mixture is heated, preferably to reflux, and the evolved water may be collected. After water evolution is completed, the solvent is removed by heating under vacuum.

In a preferred method, the DMAPA is charged to a clean, dry reactor equipped with a vent line, along with a desired amount of a hydrophobic solvent, for example an aliphatic solvent; as a particular example, isoparaffin, and the paraformaldehyde is charged in increments of 20% of the desired amount, every 15 or 20 minutes, with mixing as needed to control the exotherm. Close the reactor and vent, and continue to mix, maintaining a temperature between 180–200° F. for 14 to 16 hours. Distill off the water; increase temperature slowly, bearing in mind the DMAPA boils at 275° F., to 310–320° F. to continue to remove water. The product is effective to remove sulfur compounds by contact from oil and gas.

In any of the methods mentioned above, the formaldehyde may be in the form of an inhibited or an uninhibited solution, and may include up to 60% or more methanol. Commercial forms of formaldehyde, such as Methyl FORMCEL (55% formaldehyde in methanol or water) or Butyl FORMCEL (40% formaldehyde in butanol), both Trademarks of Celanese Corporation, may be used.

A preferred method of making my 1,3,5 ($2H_2$, $4H_2$, $6H_2$) tripropanediamine N,N,N',N',N'',N'' hexamethyl is to autocondense the compound $(CH_3)_2N\ CH_2\ CH_2\ CH_2\ N=CH_2$. This may be done in the presence of paraformaldehyde, which, it is believed, acts as a catalyst. In this reaction, no water is coproduced:

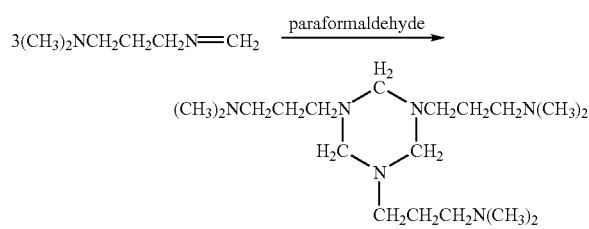

Following are examples of the use of 1,3,5 ($2H_2$, $4H_2$, $6H_2$) tripropanediamine N,N,N',N',N'',N'' hexamethyl to remove sulfur compounds from hydrocarbons:

The triazine can be added directly to a hydrocarbon stream, gas, compressed liquid such as butane or propane, or to liquids such as crude oil or fuel oil; also gasoline, Diesel oil, kerosene or bunker oil to scavenge hydrogensulfide and other sulfur compounds without water being present. The triazine may be added to oil based drilling muds where only emulsified water is present and oil is the continuous phase.

Thus it is seen that my invention is a method of treating a hydrocarbon to remove sulfur compounds from the hydrocarbon comprising adding 1,3,5 ($2H_2$, $4H_2$, $6H_2$) tripropanediamine N,N,N',N',N'',N'' hexamethyl to the hydrocarbon in the presence of water. While the triazine itself is oil soluble, a reaction product of the triazine and the sulfur compound is drawn into the water, thereby separating the hydrocarbon from the water containing the reaction product. The sulfur compound may be a sulfide (for example, hydrogen sulfide), a mercaptan, or a dialkyl disulfide such as dimethyl disulfide. The hydrocarbon may be a liquid such as crude petroleum, for example, or a gas such as natural gas or a gas which emanates from an aerobic sewage plant, a landfill, coal gas recovery systems, digester effluents, or a compost pile, and may contain from 1 ppm to 10% by weight sulfide compound. It may be used in a tower or a tank. The triazine may be added to the hydrocarbon in an amount from 1 part per million to 10% by weight; the water may preferably be present in an amount from 10% to 200% of the weight of the triazine. The water containing the sulfur compound may be separated from the hydrocarbon by any known method—for example, decanting or centrifuging.

The invention claimed is:

1. A method for treating a liquid hydrocarbon to remove a sulfur compound therefrom, comprising:
   adding 1,3,5-($2H_2$, $4H_2$, $6H_2$) tripropanediamine N,N,N', N',N'',N'' hexamethyl triazine to the liquid hydrocarbon and water to form a reaction product of the triazine and the sulfur compound that is drawn into the water; and
   separating the liquid hydrocarbon from the water containing the reaction product.

2. The method of claim 1, wherein the liquid hydrocarbon comprises a substance selected from the group consisting of crude oil, crude petroleum, petroleum, fuel oil, gasoline, diesel oil, kerosene, bunker oil, liquid propane, and liquid butane.

3. The method of claim 1, wherein 1 ppm to 10% by weight of the triazine is added to the liquid hydrocarbon, based on the weight of the liquid hydrocarbon.

4. The method of claim 1, wherein the liquid hydrocarbon comprises 1 ppm to 10% by weight of the sulfur compound and from 1 ppm to 10% by weight of the triazine is added to the liquid hydrocarbon.

5. The method of claim 3, wherein the water is used at an amount within a range from 10% to 200% of the weight of the triazine.

6. The method of claim 1, wherein the water containing the reaction compound is separated from the liquid hydrocarbon by a decanting process or a centrifuging process.

7. The method of claim 4, wherein the sulfur compound comprises a compound selected from the group consisting of hydrogen sulfide, mercaptan, dialkyl disulfide, dimethyl disulfide, and derivatives thereof.

8. A method for treating a liquid hydrocarbon to remove at least one sulfur compound therefrom, comprising:
   combining at least 1,3,5-($2H_2$,$4H_2$,$6H_2$) tripropanediamine N,N,N',N',N'',N'' hexamethyl triazine, water, and the liquid hydrocarbon to form a reaction product of the triazine and the at least one sulfur compound, wherein the reaction product is water soluble; and
   separating the liquid hydrocarbon from the water containing the reaction product.

9. A method for treating a liquid hydrocarbon to remove at least one sulfur compound therefrom, comprising:

combining at least 1,3,5-($2H_2$,$4H_2$,$6H_2$) tripropanediamine N,N,N',N',N",N" hexamethyl triazine, water, and the liquid hydrocarbon containing the at least one sulfur compound to form a reaction product of the triazine and the at least one sulfur compound that is drawn into the water; and separating the liquid hydrocarbon from the water containing the reaction product by a decanting process or a centrifuging process.

10. The method of claim 8, wherein the at least one sulfur compound is selected from the group consisting of hydrogen sulfide, mercaptan, dialkyl disulfide, dimethyl disulfide, and derivatives thereof.

11. The method of claim 8, wherein the liquid hydrocarbon comprises a substance selected from the group consisting of petroleum, crude petroleum, crude oil, fuel oil, gasoline, diesel oil, kerosene, bunker oil, liquid propane, and liquid butane.

12. The method of claim 11, wherein the water containing the reaction product is separated from the liquid hydrocarbon by a decanting process or a centrifuging process.

13. The method of claim 9, wherein the at least one sulfur compound is selected from the group consisting of hydrogen sulfide, mercaptan, dialkyl disulfide, dimethyl disulfide, and derivatives thereof.

14. The method of claim 11, wherein the triazine is combined with the liquid hydrocarbon at an amount within a range from about 1 ppm to about 10% by weight, based on the weight of the liquid hydrocarbon.

15. The method of claim 14, wherein the water is used at an amount within a range from about 10% to about 200% by weight, based on the weight of the triazine.

16. The method of claim 10, wherein the liquid hydrocarbon comprises about 1 ppm to about 10% by weight of the sulfur compound.

17. The method of claim 9, wherein the triazine is combined with the liquid hydrocarbon at an amount within a range from about 1 ppm to about 10% by weight, based on the weight of the liquid hydrocarbon.

18. The method of claim 17, wherein the water is used at an amount within a range from about 10% to about 200% by weight of the weight of the triazine.

19. The method of claim 13, wherein the liquid hydrocarbon comprises about 1 ppm to about 10% by weight of the sulfur compound.

20. A method for treating a liquid hydrocarbon to remove at least one sulfur compound therefrom, comprising:

combining at least 1,3,5-($2H_2$,$4H_2$,$6H_2$) tripropanediamine N,N,N',N',N",N" hexamethyl triazine, water, and the liquid hydrocarbon containing the at least one sulfur compound to form a reaction product of the triazine and the at least one sulfur compound that is drawn into the water, wherein the triazine is combined with the liquid hydrocarbon at an amount within a range from about 1 ppm to about 10% by weight of the weight of the liquid hydrocarbon; and separating the liquid hydrocarbon from the water containing the reaction product.

21. The method of claim 20, wherein the water is used at an amount within a range from about 10% to about 200% by weight of the weight of the triazine.

22. The method of claim 21, wherein the liquid hydrocarbon comprises about 1 ppm to about 10% by weight of the sulfur compound.

23. The method of claim 16, wherein the liquid hydrocarbon comprises a substance selected from the group consisting of crude oil, crude petroleum, petroleum, fuel oil, gasoline, diesel oil, kerosene, bunker oil, liquid propane, and liquid butane.

24. The method of claim 20, wherein the liquid hydrocarbon comprises a substance selected from the group consisting of crude oil, crude petroleum, petroleum, fuel oil, gasoline, diesel oil, kerosene, bunker oil, liquid propane, and liquid butane.

25. The method of claim 20, wherein the water containing the reaction product is separated from the liquid hydrocarbon by a decanting process or a centrifuging process.

\* \* \* \* \*

UNITED STATES PATENT AND TRADEMARK OFFICE
CERTIFICATE OF CORRECTION

| | | |
|---|---|---|
| PATENT NO. | : 7,211,665 B2 | Page 1 of 1 |
| APPLICATION NO. | : 10/291461 | |
| DATED | : May 1, 2007 | |
| INVENTOR(S) | : Larry W. Gatlin | |

It is certified that error appears in the above-identified patent and that said Letters Patent is hereby corrected as shown below:

In the Claims:

In Column 6, Claim 23, Line 26, please delete "16" and insert --17--.

Signed and Sealed this

Twenty-first Day of August, 2007

JON W. DUDAS
*Director of the United States Patent and Trademark Office*